United States Patent
Widt

(10) Patent No.: US 9,933,325 B2
(45) Date of Patent: Apr. 3, 2018

(54) PICO TEST LEAK

(71) Applicant: Inficon GmbH, Cologne (DE)

(72) Inventor: Rudi Widt, Cologne (DE)

(73) Assignee: Inficon GmbH, Cologne (DE)

( * ) Notice: Subject to any disclaimer, the term of this patent is extended or adjusted under 35 U.S.C. 154(b) by 72 days.

(21) Appl. No.: 14/911,872

(22) PCT Filed: Aug. 13, 2014

(86) PCT No.: PCT/EP2014/067309
§ 371 (c)(1),
(2) Date: Feb. 12, 2016

(87) PCT Pub. No.: WO2015/024831
PCT Pub. Date: Feb. 26, 2015

(65) Prior Publication Data
US 2016/0195448 A1    Jul. 7, 2016

(30) Foreign Application Priority Data
Aug. 20, 2013 (DE) .................. 10 2013 216 450

(51) Int. Cl.
G01N 33/00  (2006.01)
G01M 3/00   (2006.01)
G01M 3/20   (2006.01)
F02D 41/14  (2006.01)
G01N 21/3504 (2014.01)

(52) U.S. Cl.
CPC .......... G01M 3/007 (2013.01); G01M 3/207 (2013.01); F02D 41/1495 (2013.01); G01N 21/3504 (2013.01); G01N 33/0006 (2013.01); G01N 33/007 (2013.01)

(58) Field of Classification Search
CPC .................................... G01N 33/0006
USPC ........................................... 73/1.06
See application file for complete search history.

(56) References Cited

U.S. PATENT DOCUMENTS

| | | | |
|---|---|---|---|
| 4,794,784 A | 1/1989 | Bley | |
| 5,417,105 A * | 5/1995 | Martinez | G01M 3/205 73/40.7 |
| 5,663,487 A | 9/1997 | Widt | |
| 6,230,549 B1 * | 5/2001 | Harris | G01M 3/025 73/40 |
| 6,595,040 B1 * | 7/2003 | Widt | G01M 3/00 73/1.02 |
| 8,074,492 B2 | 12/2011 | Brockmann | |

(Continued)

FOREIGN PATENT DOCUMENTS

| | | |
|---|---|---|
| DE | 3243752 A1 | 5/1984 |
| DE | 4038266 A1 | 6/1992 |

(Continued)

OTHER PUBLICATIONS

International Search Report, PCT/EP2014/067309, dated Nov. 19, 2014, 3 pages.*

(Continued)

Primary Examiner — Clayton E Laballe
Assistant Examiner — Kevin Butler
(74) Attorney, Agent, or Firm — The Webb Law Firm

(57) ABSTRACT

Test leak device including a gas-filled container and a capillary extending through a container wall. The gas including at least 10% of atmospheric air.

13 Claims, 1 Drawing Sheet

(56) References Cited

U.S. PATENT DOCUMENTS

| | | | | |
|---|---|---|---|---|
| 2015/0276541 A1* | 10/2015 | Decker | ................ | G01M 3/007 |
| | | | | 73/1.58 |
| 2015/0362419 A1* | 12/2015 | Chertov | ............... | G01N 15/088 |
| | | | | 73/38 |
| 2016/0195448 A1* | 7/2016 | Widt | .................... | G01M 3/207 |
| | | | | 73/1.06 |

FOREIGN PATENT DOCUMENTS

| | | | | |
|---|---|---|---|---|
| DE | 19906941 | * | 8/2000 | ............. G01M 3/00 |
| DE | 19906941 A1 | | 8/2000 | |
| DE | 102006016747 A1 | | 10/2007 | |
| DE | 102009012213 A1 | | 9/2010 | |
| DE | 102010050505 A1 | | 5/2012 | |
| EP | 0110004 A1 | | 6/1984 | |
| EP | 0242684 A2 | | 10/1987 | |
| EP | 0352371 | * | 11/1988 | ............. G01M 3/04 |
| EP | 0352371 A2 | | 1/1990 | |
| EP | 0742894 B1 | | 1/1995 | |
| EP | 1637861 | * | 9/2004 | ............. G01M 3/20 |
| EP | 1637861 A1 | | 3/2006 | |

OTHER PUBLICATIONS

Written Opinion International Search Authority, PCT/EP2014/067309, dated Nov. 19, 2014, 8 pages.*

* cited by examiner

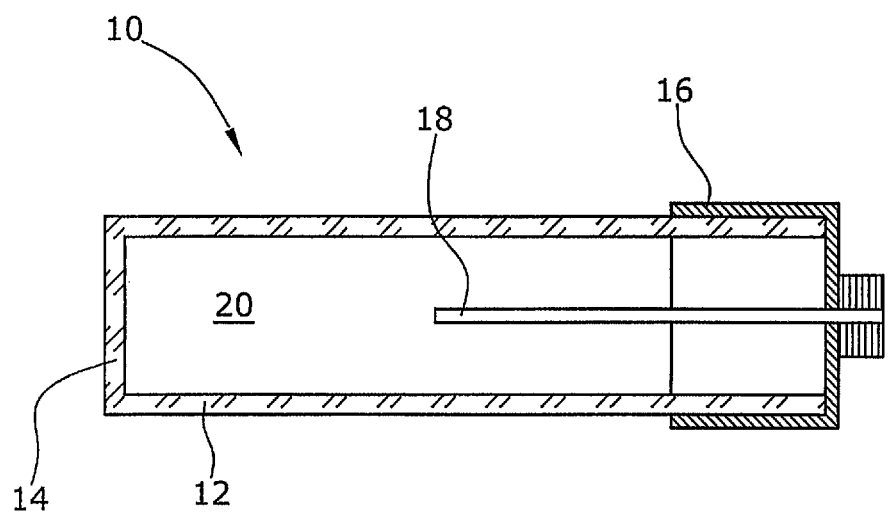

PICO TEST LEAK

CROSS-REFERENCE TO RELATED APPLICATIONS

This application is the United States national phase of International Application No. PCT/EP2014/067309 filed Aug. 13, 2014, and claims priority to German Patent Application No. 10 2013 216 450.5 filed Aug. 20, 2013, the disclosures of which are hereby incorporated in their entirety by reference.

BACKGROUND OF THE INVENTION

Field of the Invention

The invention relates to a test leak device for testing and calibrating a gas leak detector.

Description of Related Art

Test leaks include a housing filled with a test gas and are provided with a leak with a predetermined known leakage rate, with which the test gas escapes to the outside. The functionality or the precision of the gas leak detector can be tested by measuring the gas escaping from the test leak.

EP 0 742 894 B1 describes a test leak provided with a capillary that achieves a comparatively low leakage rate of $10^{-7}$ mbar·l/s or more. Such capillaries cannot be made infinitely small, since they would then become occluded due to air humidity and thus be useless. Up to the present day, it has been impossible to achieve leakage rates of $10^{-12}$ mbar·l/s or less with known test leaks. Such leakage rates are required to test leak test devices for very small leaks.

SUMMARY OF THE INVENTION

It is an object of the invention to provide a test leak with a low leakage rate in the region of $10^{-12}$ mbar·l/s.

The test leak device of the present invention includes a container filled with a gas with at least 10% atmospheric air. The remaining proportion of the gas may be nitrogen, for instance. The container wall is penetrated by at least one capillary. The capillary should have a leakage rate in the range of about $10^{-5}$ mbar·l/s to $10^{-7}$ mbar·l/s and preferably $10^{-6}$ mbar·l/s. Atmospheric air does not cause an occlusion of the capillary and typically has a proportion of helium and a proportion of argon. Helium and argon are typical test gases used in gas leak detection. The proportion of helium in the air in the container should be in a range from three to seven ppm and preferably about 3.5 to 5.5 ppm. A particularly proportion of helium is about 5 ppm. In the present description the term "about" means a respective deviation of ±10%. The proportion of argon in the air in the container should be in a range from 0.1 to 2% and preferably about 0.8 to 1.2%. A particularly advantageous proportion of argon is about 1%.

Filling the test leak container with atmospheric air further makes a separate filling nozzle at the test leak obsolete, which nozzle would increase the outer dimensions and make it more difficult to use in small test chambers.

It is particularly advantageous if the container is a cylinder with a cover on a front end side or with an end cap. The end cap is penetrated by the capillary. The cylinder should not exceed a length of 5 cm and a diameter of about 1 cm. The capillary may be guided within the cylinder along the central axis thereof. It is particularly advantageous if the container is made of glass and the end cap is made of a metal. Such a container may also be used in particularly small test chambers and can be filled in a simple manner. Filling is performed simply by removing the end cap and by the gas flowing into the container together with the atmospheric air. The cylindrical test leak container has a small surface area and may be evacuated in a simple manner in a test chamber due to the absence of gaps or recesses.

The gas in the container should have a relative air humidity of less than 50% and preferably less than 40% so as to avoid occlusion of the capillary by air humidity.

BRIEF DESCRIPTION OF THE DRAWING

An embodiment will be explained hereunder with reference to the drawing.

FIG. 1 shows a longitudinal cross-section through a test leak device according to the present disclosure.

DETAILED DESCRIPTION OF THE INVENTION

The test leak device 10 includes a cylindrical container 12 of glass with a closed bottom 14 at one end face and an open end at the opposite end face. The open end is tightly closed with an end cap 16 of metal. A capillary 18 is guided through the metal cap 16 along the longitudinal central axis of the cylinder 12.

The container 12 is filled with atmospheric air 20 having a proportion of helium of 5 ppm and a proportion of argon of 1%. The capillary 18 has a leakage rate of $10^{-6}$ mbar·l/s. The humidity of the air is about 40%. For the test leak device 10, this results in an effective gas flow of:

$$1 \cdot 10^{-6} \text{ mbar·l/s} \cdot 5 \text{ ppm} = 5 \cdot 10^{-12} \text{ mbar·l/s for helium}$$

and $$1 \cdot 10^{-6} \text{ mbar·l/s} \cdot 1\% = 1 \cdot 10^{-8} \text{ mbar·l/s for argon.}$$

While an embodiment of the test leak device 10 is provided in the foregoing description, those skilled in the art may make modifications and alterations to this embodiment without departing from the scope and spirit of the disclosure. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A method of using a gas-filled container as a test leak device for testing and calibrating a gas leak detector, the method comprising:
   providing a capillary having a known predetermined leakage rate by which a gas penetrates to outside of the container, the capillary penetrating a container wall of the gas-filled container and extending into the interior of the gas-filled container;
   providing at least a 10% volumetric proportion of atmospheric air in the gas within the gas-filled container; and
   measuring the gas escaping through the capillary with the gas leak detector, thereby testing a functionality or a precision of the gas leak detector.

2. The method of claim 1, wherein the capillary has a leakage rate of at most $10^{-6}$ mbar·l/s.

3. The method of claim 1, wherein the atmospheric air has a relative humidity of less than 50%.

4. The method of claim 3, wherein the atmospheric air has a relative humidity of less than 40%.

5. The method of claim 1, wherein a proportion of helium in the atmospheric air is in a range from 3 to 7 ppm.

6. The method of claim 5, wherein the proportion of helium in the atmospheric air is in a range from 4.5 to 5.5 ppm.

7. The method of claim 1, wherein a proportion of argon in the atmospheric air is about 0.5% to 2%.

8. The method of claim 7, wherein the proportion of argon in the atmospheric air is about 0.8% to 1.2%.

9. The method of claim 1, wherein the container is cylindrical with a removable end cap through which the capillary is guided.

10. The method of claim 9, wherein the cylinder is made of glass.

11. The method of claim 9, wherein the removable end cap is made of a metal.

12. The method of claim 9, wherein the container has a length of 5 cm at most and a diameter of 1 cm at most.

13. The method of claim 12, wherein the container has a length of about 4 cm and a diameter of about 0.8 cm.

* * * * *